United States Patent [19]
Meo et al.

[11] Patent Number: 5,879,886
[45] Date of Patent: Mar. 9, 1999

[54] METHOD FOR DETECTING MOLECULES CONTAINING NUCLEOTIDE MISMATCHES AND THE LOCATION OF THESE MISMATCHES, AND APPLICATION TO THE DETECTION OF BASE SUBSTITUTIONS OR DELETIONS IN NUCLEOTIDE SEQUENCES

[75] Inventors: Tommaso Meo, Paris; Mario Tosi, Maisons-Alfort; Elisabeth Verpy, Saint-Maurice; Michel Biasotto, Juvisy-sur-Orge, all of France

[73] Assignees: Institut Pasteur; Institut National de la Sante et de la Recherche Medicale, both of Paris, France

[21] Appl. No.: 605,163

[22] PCT Filed: Sep. 9, 1994

[86] PCT No.: PCT/FR94/01068

§ 371 Date: Jul. 15, 1996

§ 102(e) Date: Jul. 15, 1996

[87] PCT Pub. No.: WO95/07361

PCT Pub. Date: Mar. 16, 1995

[30] Foreign Application Priority Data

Sep. 10, 1993 [FR] France ................... 93/10821

[51] Int. Cl.⁶ .............. C12Q 1/68; C12P 19/34; C12N 9/16
[52] U.S. Cl. .............. 435/6; 435/91.2; 435/196; 536/24.3; 935/77; 935/78
[58] Field of Search .............. 435/6, 91.2, 196; 935/72, 78; 536/24.3

[56] References Cited

U.S. PATENT DOCUMENTS

| | | | |
|---|---|---|---|
| 5,217,863 | 6/1993 | Cotton et al. | 435/6 |
| 5,376,526 | 12/1994 | Brown et al. | 435/6 |
| 5,556,750 | 9/1996 | Modrich et al. | 435/6 |

FOREIGN PATENT DOCUMENTS

| | | |
|---|---|---|
| 0 317 239 | 5/1989 | European Pat. Off. . |
| WO 89/11548 | 11/1989 | WIPO . |
| WO 90/13668 | 11/1990 | WIPO . |
| WO 93/02216 | 2/1993 | WIPO . |

OTHER PUBLICATIONS

Wood et al., "HLA–DR/Dw Matching By PCR Fingerprinting: The Origin of PCR Fingerprints and Further Applications", *European J. of Immunogenetics,* vol. 18, pp. 147–153 (1991).

Friedl et al., "Single–step Screening Method for the Most Common Mutation in Familial Adenomatous Polyposis," *Human Molecular Genetics,* vol. 2, No. 9, pp. 1481–1482 (1993).

Cai et al., "A Rapid and Simple Electrophoretic Method for the Detection of Mutations . . . ", *Human Genetics,* vol. 87, No. 6, pp. 728–730 (1991).

Lu et al., "Detection of Single DNA Base Mutations with Mismatch Repair Enzymes," *Genomics,* vol. 14, No. 2, pp. 249–255 (1992).

R. Cotton, "Current Methods of Mutation Detection," *Mutation Research,* vol. 285, pp. 125–144 (1993).

Myers et al., *Methods Enzymol,* vol. 155, pp. 501–527 (1987).

Orita et al., *Genomics,* vol. 5, p. 874 (1989).

Cotton et al., *Proc. Nat'l Acad. Scie., USA,* vol. 85, pp. 4397–4401 (1988).

*Primary Examiner*—Stephanie W. Zitomer
*Attorney, Agent, or Firm*—Finnegan, Henderson, Farabow, Garrett & Dunner

[57] ABSTRACT

Method for the detection and/or location of mutations or deletions in nucleotide sequences by creation of heteroduplexes between two types of double-stranded DNA able to form mismatches at the sites of said mutations or deletions. The heteroduplexes are detected as a result of the labeling of each type of strand by different fluorescent molecules or are screened by passage over a support which specifically retains them.

25 Claims, 7 Drawing Sheets

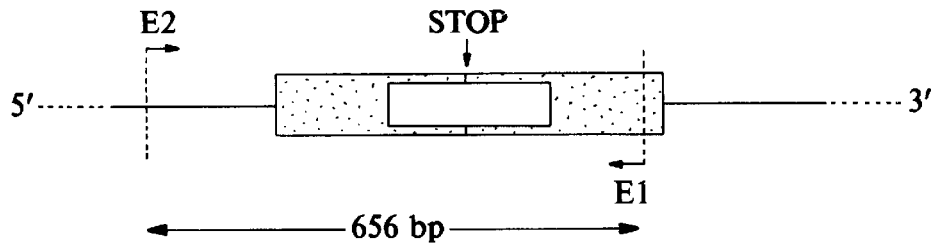

FIG. 1A

```
(SEQ ID NO:21)  AA TTC TTC GAT TTT TCT TAT GAC CTT AAC CTG TGT GGG
(SEQ ID NO:22) Glu Phe Phe Asp Phe Ser Tyr Asp Leu Asn Leu Cys Gly

CTG ACA GAG GAC CCA GAT CTT CAG GTT TCT GCG ATG CAG CAC CAG ACA
Leu Thr Glu Asp Pro Asp Leu Gln Val Ser Ala Met Gln His Gln Thr

GTG CTG GAA CTG ACA GAG ACT GGG GTG GAG GCG GCT GCA GCC TCC GCC
Val Leu Glu Leu Thr Glu Thr Gly Val Glu Ala Ala Ala Ala Ser Ala

C340    ③316⃝
                                    C,T320 C317          C,T350
ATC TCT GTG GCC CGC ACC CTG CTG GTC TTT GAA GTG CAG CAG CCC TTC
Ile Ser Val Ala Arg Thr Leu Leu Val Phe Glu Val Gln Gln Pro Phe
                                               A   G          C
                                              Met  Glu        Ser
                                              451  452        455

ⓘ  C,T362
      ③57⃝ T362       ③69⃝   ②83⃝          C386
         C,T299 C295                       C271
CTC TTC GTG CTC TGG GAC CAG CAG CAC AAG TTC CCT GTC TTC ATG GGG
Leu Phe Val Leu Trp Asp Gln Gln His Lys Phe Pro Val Phe Met Gly
     A   C                                         G
    Met Pro                                       Arg
    458  G                                        467

Arg
            459
C,T400       C,T412
CGA GTA TAT GAC CCC AGG GCC TGA
Arg Val Tyr Asp Pro Arg Ala
 T            T
Stop         Ser
472          476
```

FIG. 1B

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

GTGAACTTGA ACTAGAGAAA GC                            22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TGAGGATCCC ACGAACTGCC AG                            22

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGGGGGAGT                                           9

( 2 ) INFORMATION FOR SEQ ID NO:4:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTTCATGCT                                           9

( 2 ) INFORMATION FOR SEQ ID NO:5:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TGAAATGCA                                           9

( 2 ) INFORMATION FOR SEQ ID NO:6:

( i ) SEQUENCE CHARACTERISTICS:
        ( A ) LENGTH: 9 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:6:

CCCTCCCTC 9

( 2 ) INFORMATION FOR SEQ ID NO:7:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GTGCTCTGG 9

( 2 ) INFORMATION FOR SEQ ID NO:8:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TGACCCCAG 9

( 2 ) INFORMATION FOR SEQ ID NO:9:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GTGCCCTGG 9

( 2 ) INFORMATION FOR SEQ ID NO:10:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AGTGCAGCA 9

( 2 ) INFORMATION FOR SEQ ID NO:11:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TTCCCTGTC 9

( 2 ) INFORMATION FOR SEQ ID NO:12:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TTCCCTGTC 9

( 2 ) INFORMATION FOR SEQ ID NO:13:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AGTGCAGCA 9

( 2 ) INFORMATION FOR SEQ ID NO:14:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GGGGTGAGT 9

( 2 ) INFORMATION FOR SEQ ID NO:15:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CTTCGTGCT 9

( 2 ) INFORMATION FOR SEQ ID NO:16:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TGACTCCAG 9

( 2 ) INFORMATION FOR SEQ ID NO:17:

( i ) SEQUENCE CHARACTERISTICS:
   ( A ) LENGTH: 9 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:17:

CCCTTCCTC                                                                                                9

( 2 ) INFORMATION FOR SEQ ID NO:18:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:18:

GTGCTCTGG                                                                                                9

( 2 ) INFORMATION FOR SEQ ID NO:19:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:19:

TGAAGTGCA                                                                                                9

( 2 ) INFORMATION FOR SEQ ID NO:20:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:20:

CACGCGACC                                                                                                9

( 2 ) INFORMATION FOR SEQ ID NO:21:

( i ) SEQUENCE CHARACTERISTICS:
      ( A ) LENGTH: 254 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:21:

AATTCTTCGA TTTTTCTTAT GACCTTAACC TGTGTGGGCT GACAGAGGAC CCAGATCTTC                60

AGGTTTCTGC GATGCAGCAC CAGACAGTGC TGGAACTGAC AGAGACTGGG GTGGAGGCGG               120

CTGCAGCCTC CGCCATCTCT GTGGCCCGCA CCCTGCTGGT CTTTGAARTG SAGCAGCCCT               180

YCCTCTTCRT GCBCTGGGAC CAGCAGCACA AGTTCCSTGT CTTCATGGGG YGAGTATATG               240

ACYCCAGGGC CTGA                                                                254

( 2 ) INFORMATION FOR SEQ ID NO:22:

( i ) SEQUENCE CHARACTERISTICS:
        ( A ) LENGTH: 84 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 57
        ( D ) OTHER INFORMATION: /note= "Xaa = Val or Met"

( i x ) FEATURE:
        ( A ) NAME/KEY: Peptide
        ( B ) LOCATION: 58
        ( D ) OTHER INFORMATION: /note= "Xaa = Gln or Glu"

( i x ) FEATURE:
        ( A ) NAME/KEY: Peptide
        ( B ) LOCATION: 61
        ( D ) OTHER INFORMATION: /note= "Xaa = Phe or Ser"

( i x ) FEATURE:
        ( A ) NAME/KEY: Peptide
        ( B ) LOCATION: 64
        ( D ) OTHER INFORMATION: /note= "Xaa = Val or Met"

( i x ) FEATURE:
        ( A ) NAME/KEY: Peptide
        ( B ) LOCATION: 65
        ( D ) OTHER INFORMATION: /note= "Xaa = Leu or Pro or Arg"

( i x ) FEATURE:
        ( A ) NAME/KEY: Peptide
        ( B ) LOCATION: 73
        ( D ) OTHER INFORMATION: /note= "Xaa = Pro or Arg"

( i x ) FEATURE:
        ( A ) NAME/KEY: Peptide
        ( B ) LOCATION: 78
        ( D ) OTHER INFORMATION: /note= "Xaa = Arg or Stop"

( i x ) FEATURE:
        ( A ) NAME/KEY: Peptide
        ( B ) LOCATION: 82
        ( D ) OTHER INFORMATION: /note= "Xaa = Pro or Ser"

( x i ) SEQUENCE DESCRIPTION: SEQ ID NO:22:

```
Glu  Phe  Phe  Asp  Phe  Ser  Tyr  Asp  Leu  Asn  Leu  Cys  Gly  Leu  Thr  Glu
 1                   5                        10                       15

Asp  Pro  Asp  Leu  Gln  Val  Ser  Ala  Met  Gln  His  Gln  Thr  Val  Leu  Glu
               20                        25                       30

Leu  Thr  Glu  Thr  Gly  Val  Glu  Ala  Ala  Ala  Ala  Ser  Ala  Ile  Ser  Val
          35                        40                       45

Ala  Arg  Thr  Leu  Leu  Val  Phe  Glu  Xaa  Xaa  Gln  Pro  Xaa  Leu  Phe  Xaa
     50                        55                       60

Xaa  Trp  Asp  Gln  Gln  His  Lys  Phe  Xaa  Val  Phe  Met  Gly  Xaa  Val  Tyr
65                        70                       75                       80

Asp  Xaa  Arg  Ala
```

METHOD FOR DETECTING MOLECULES CONTAINING NUCLEOTIDE MISMATCHES AND THE LOCATION OF THESE MISMATCHES, AND APPLICATION TO THE DETECTION OF BASE SUBSTITUTIONS OR DELETIONS IN NUCLEOTIDE SEQUENCES

This application is a 371 (National Stage) of PCT/FR94/01068 filed Sep. 9, 1994 which claims priority to the French application, 93/10821, filed Sep. 10, 1993.

The object of the present invention is a method for detecting molecules containing nucleotide mismatches and the location of these mismatches, and its application to the detection of base substitutions or deletions in nucleotide sequences.

BACKGROUND OF THE INVENTION

The majority of diseases linked to with genome modifications, either of the host organisms or of infectious organisms, are very often due to a simple change of one or more nucleotides. Considerable effort has therefore been devoted to develop methods for detecting not only already known mutations but also unknown mutations.

However, the methods available for searching for unknown point mutations in DNA regions of significant size have many disadvantages which render their use difficult.

For example, electrophoresis gels with a denaturation gradient require computer-assisted optimizations of the target region and electrophoresis conditions adapted to each DNA fragment (Myers et al. (1987), Methods Enzymol, 155, 501–527).

The technique of single strand conformation polymorphism (SSCP) (Orita et al. (1989)—Genomics, 5, 874), despite its experimental simplicity, has shown a sensitivity for the detection of mutations in DNA fragments of around 150 base pairs.

However, neither of these methods gives precise information concerning the location of the mutation in the DNA fragment.

Although direct sequencing methods are becoming increasingly rapid, they remain costly and lengthy in searching for unknown mutations and are not reliable in the case of heterozygous point mutations.

Another method involving chemical cleavage at the site of the mismatches (CCM) such as described by Cotton et al. (Proc. Natl. Acad. Sci., USA (1988) 85, 4397–4401) is in principle well suited to the detection of mutations, independently of the length and the composition of the sequence of the region of interest. It has been used with success in a large number of studies (Cotton (1993) Mutation Research 285, 125–144).

This method has enabled the detection of mutations in fragments amplified by enzymatic routes and of a length of one kilobase.

No present method is likely to be used routinely for various reasons: lack of reliability (a significant number of false negatives) and also because the complexity of the methods which thus do not lend themselves to automated operation.

For example in the conventional CCM method, the heteroduplexes, in other words the double-stranded DNA, resulting from a matching between two heterologous DNA molecules, are formed between the patient's DNA amplified by the enzymatic route, and a DNA fragment representing the wild type sequence labeled at one end by use of a radioactive isotope. The heteroduplex DNA molecules are formed with the DNA corresponding to the sequence of the wild type labeled at the ends of each of its strands, coding or non-coding, and are then chemically treated in parallel reactions in order to reveal the mismatches.

In theory, all the mutations ought to be able to be detected by the use of two probes, after specific cleavage of the non-matched cytosines and thymines induced by hydroxylamine and osmium tetroxide respectively, since a non-matched cytosine or thymine should be present at the site of the mutation, either on the coding strand or on the non-coding strand of the probe labeled with a radioactive isotope.

In practice, cleavage at the site of some mismatches can occur incorrectly, because of the nature of the non-matched bases and the environment of these bases.

The probes used in the conventional CCM method thus do not allow for four types of heteroduplex existing simultaneously. For example, Cotton et al. (1993, cited above) describe only one or two types of heteroduplex.

A further disadvantage of this technique is the necessity for repeating the radioactive labeling of the primers for chain polymerization (PCR) and the size markers.

In addition, this technique requires the preparation of a double series of heteroduplexes, with terminal labeling of the sense strand and nonsense strand in order to detect separately the bases modified on one strand or the other.

Finally, the CCM method does not lead to the detection of all the heteroduplexes and thus does not allow the detection of some mutations.

A probe is defined as a labeled nucleotide sequence comprising a sufficient number of nucleotides to establish the specific complementarity between this sequence and the sequence present in the sample.

For example, a probe used according to the invention can consist of between 8 and 2 000 nucleotides.

A heteroduplex is defined as a DNA strand hybridized with a complementary strand containing at least one mismatch or one deletion or non-matched loop.

The applicants have thus endeavored to develop a more reliable, more rapid technique which can be automated, enabling an unambiguous determination of the base substitution, consisting of a smaller number of steps, and using non-radioactive labels.

SUMMARY OF THE INVENTION

The applicants have thus shown unexpectedly that it is possible to detect and locate, in a more rapid and more reliable manner, base substitutions in the nucleotide sequences by labeling each of the sense and nonsense strands with a fluorescent or enzymatic label.

The use of fluorescent labels is also an advantage as regards the general conditions of implementation of the method, as much from the point of view of safety as from the point of view of apparatus. It also allows the use of different labels for each strand, without this double labeling involving technical or material difficulties, as would be the case in carrying out a double radioactive labeling.

The applicants have additionally shown that the base deletions or substitutions can be rapidly detected by screening the heteroduplexes on a support which specifically retains them.

The applicants have also shown that, in the case of heterozygous mutations, the base substitutions can be detected solely from the amplified DNA of the sample to be analyzed, without the involvement in the reaction of a DNA originating from homozygous individuals having the wild type allele.

This particular embodiment of the invention thus avoids having to prepare a labeled wild type DNA, eliminates a step in the reaction and reduces the costs. The implementation of this preferred embodiment thus only requires the use of a sample of the DNA to be analyzed.

The general object of the present invention is the detection and/or location of mutations or deletions in nucleotide sequences by creation of heteroduplexes between two types of double-stranded DNA able to form mismatches at the sites of said mutations and deletions.

According to a first embodiment, the heteroduplexes are detected as a result of the labeling of each type of strand, sense and nonsense, by different fluorescent molecules.

According to a second embodiment, the DNA's are not labeled and the heteroduplexes are screened by passage over a support which specifically retains them.

The object of the present invention is thus, according to the first embodiment, a method for detecting the presence and the position of base substitutions or deletions in a nucleotide sequence contained in a preparation of double-stranded DNA to be tested in which:

the region containing the nucleotide sequence of on the one hand the DNA to be tested and on the other a DNA of known sequence is specifically amplified, and the sense and nonsense strands of these DNA's are labeled with different fluorescent labels or non-isotopic labels, the amplified DNA's are hybridized, and the heteroduplexes formed are detected.

Advantageously, the DNA to be tested and the known DNA are amplified in the same preparation.

Another object of the invention is a method for detecting the presence and the position of base substitutions or deletions in a nucleotide sequence contained in a preparation of heterozygous or heterogenous double-stranded DNA to be tested in which:

the region containing the nucleotide sequence of the DNA to be tested is specifically amplified and the sense and nonsense strands of this DNA are labeled with different fluorescent labels or non-isotopic labels, the amplified DNA's are hybridized, and the heteroduplexes formed are detected.

Advantageously, the heterogenous DNA is composed of a mixture of DNA from two variants of a bacteria or of DNA extracted from tumor mosaic cells.

According to a particular embodiment, the samples of double-stranded DNA containing the nucleotide sequence to be determined are amplified by the chain polymerization method using two primers located at the two ends of the sequence to be amplified.

The two primers can be labeled respectively with different fluorescent labels.

The double-stranded DNA to be determined advantageously has a size of between 150 and 10,000 base pairs.

The heteroduplexes are preferably detected by cleavage of the non-matched parts of the strands.

The hybridization step is carried out, according to a method known in the state of the art, by denaturation and renaturation of the amplified DNA, which allows formation of mismatched molecules if the DNA contains, in the heterozygous state (genetic diseases) or heterogeneously in the cellular mosaic state (tumor mass mixed with healthy cells in various proportions), one or more mutations (deletions or substitutions).

In the case where the DNA in which the mutation is sought originates from a haploid cell, the heteroduplex molecules form if the amplification of a mixture of the two types of DNA, wild and mutant, has been performed.

Preferably, the reagent cleaving the non-matched parts is a chemical reagent, such as hydroxylamine, osmium tetroxide or potassium permanganate or an enzyme such as MutY (Lu and Chang, (1992), Genomics, 14, 249–255) or one of the enzymes, endonucleases and glycosylases, described by Chang and Lu in 1991 (Nucleic Acid Res., 19, 4791–4766), by Chehabet and Kan in 1989 (Proc. Natl. Acad. Sci., USA, 86, 9178–9182, by Hennecke et al. in 1991 (nature, 353, 776–778), by Nickerson et al. in 1990 (Proc. Natl. Acad. Sci., USA, 87, 8923–8927), by Wieabauer and Jiricny in 1990 (Proc. Natl. Acad. Sci., USA, 87, 5842–5845) or by Yeh et al. in 1991 (J. Biol. Chem., 266, 6480–6484).

They may also be detected by a biophysical method enabling them to be differentiated from homoduplexes, such as chromatography or electrophoresis.

Advantageously, the heteroduplexes are, prior to their detection, concentrated by passage over a support which specifically retains them.

According to the second embodiment, the object of the invention is a method for detecting the presence of base substitutions or deletions in a nucleotide sequence contained in a preparation of double-stranded DNA to be tested in which:

the region containing the nucleotide sequence of on the one hand the DNA to be tested and on the other a DNA of known sequence is specifically amplified, the amplified DNA's are hybridized, and the heteroduplexes formed are detected by passage over a support which specifically retains them.

Another object is a method for detecting the presence of base substitutions or deletions in a nucleotide sequence contained in a preparation of heterozygous or heterogenous double-stranded DNA to be tested in which:

the region containing the nucleotide sequence of the DNA to be tested is specifically amplified, the amplified DNA's are hybridized, and the heteroduplexes formed are detected by passage over a support which specifically retains them.

Preferably, said support carries a protein specifically binding the heteroduplexes, such as MutS. The heteroduplexes retained are revealed by a molecule specifically attaching itself to the DNA, such as ethidium bromide or by any other means within the capability of a person skilled in the art, such as fluorescence or radioactivity.

Said support can be composed of beads, spheres or particles or be the wall of a microplate well for biochemical testing, covered with anti-MutS antibody.

The present invention is particularly suited to the detection of base substitutions in patients suffering from hereditary diseases, such as angioedema, hemoglobinopathy, mucoviscidosis, muscular dystrophy and in patients suffering from cancerous diseases such as breast cancer, leukemia, colonic cancer and diseases linked to effects of oncogenic or antioncogenic sequences.

The advantage of the second embodiment of the invention lies in the fact that it permits the rapid screening of a large number of DNA preparations, for example a population.

Although it enables a mutation to be detected, it does not locate it, which may however be carried by the method according to the first embodiment.

An additional object of the present invention is a composition comprising at least three probes able to form heteroduplexes with nucleic sequences in which the presence or absence of point mutations is sought.

A final object is heteroduplexes combined with a complex consisting of a molecule of type MutS and an anti-MutS antibody.

The present invention can readily be used by a person skilled in the art using his general knowledge in the field of biology, and in particular in the field of chain polymerization.

General information more specifically relating to the techniques necessary to perform the methods which are the objects of the present invention can in particular be found in "PCR Protocols. A guide to methods and application" (Innis et al., Academic Press Inc., Harcourt Brace Jovanovich Publishers, 1990).

BRIEF DESCRIPTION OF THE DRAWINGS

The present invention is illustrated without in any way being limited by the following examples in which.

DETAILED DESCRIPTION OF THE INVENTION

Materials and methods

DNA samples

Figure 2A:
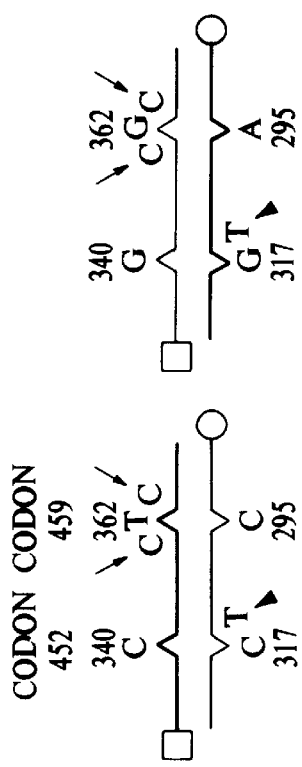
FIG. 2A schematically shows the different heteromatches able to take place in the regions of codons 452 and 459, FIGS. 2B and 2C respectively represent the fluorescence intensity of different oligonucleotides obtained after, respectively, treatment with hydroxylamine and osmium tetroxide of the hybridization products between the wild and mutant alleles corresponding to the regions containing codons 452 and 459, FIG. 3A schematically shows the heteromatches able to take place in the regions of codons 458 and 467.

Thirty-six unrelated patients suffering from angioedema for whom analysis by membrane hybridization techniques (blot) had not detected genic alterations were studied, and the tests were related to point mutations in exon 8 using the conventional CCM method (Cotton et al., (1988), Proc. Natl. Acad. Sci. USA 85, 4397–4401) and the DNA sequencing method.

Preparation of probes labeled with fluorescent labels

Oligonucleotide primers were synthesized on a Beckman 200A DNA synthesizer or an Applied Biosystem 392 (ABI) DNA/RNA synthesizer.

One microgram of genomic DNA isolated from peripheral blood leukocytes was amplified by the chain polymerization technique (PCR) in a reaction medium of 100 µl, using E1 and E2 oligonucleotide primers, as shown in FIG. 1A.

The reaction was carried out for 30 to 35 cycles. The probe labeled by fluorescence was obtained by re-amplification, over 25 cycles, using 2 µl of the product from the first amplification reaction and using the same primers made fluorescent by coupling of an ester of a dye and of N-hydroxysuccinimide to an aminohexyl coupler attached to the 5' end according to the ABI protocol.

The sequence of the E1 oligonucleotide, which was labeled with the JOE fluorophore is: 5'-GTG AAC TTG AAC TAG AGA AAG C-3 (SEQ ID NO: 1).

The sequence of the E2 oligonucleotide, which was labeled with the FAM fluorophore, is: 5'-TGA GGA TCC CAC GAA CTG CCA G-3' (SEQ ID NO: 2).

Heteroduplex formation and chemical cleavage of the mismatches

The fragments amplified by chain polymerization and doubly labeled were precipitated with ethanol. The DNA quantities were estimated on an agarose gel and 450 ng of DNA were used in order to form the heteroduplexes. The samples were brought to the boil over 5 minutes in 150 µl of 1.3M NaCl/3.5 mM $MgCl_2$/3 mM Tris-HCl, pH 7.7, chilled in ice for 5 minutes then incubated overnight at 42° C.

After hybridization, the samples were precipitated with ethanol and resuspended in 18 µl of water.

The general procedure for performing the chemical cleavage of the mismatches has been described by Cotton et al. ((1988) Proc. Natl. Acad. Sci. USA 85, 4397–4401).

6 µl of the DNA heteroduplex were used for each chemical modification. 5 ml of 7M hydroxylamine hydrochloride were prepared in distilled water for each experiment and 4 ml were brought to pH 6 by addition of diethylamine.

6 µl of DNA were treated with 20 µl of a hydroxylamine solution at 37° C. for from 45 minutes to 1 hour. The final hydroxylamine concentration was approximately 3.8M.

The osmium tetroxide (4% by weight of aqueous solution) was diluted in distilled water to obtain a standard 1% solution and aliquots were stored at −80° C. in siliconed tubes.

6 µl of DNA were incubated for 15 minutes at ambient temperature in a solution of 0.4% osmium tetroxide/2% pyridine/0.5 mM Hepes, pH 8/0.5 mM $Na_2EDTA$ in a total volume of 25 µl in siliconed tubes.

The reactions were stopped by transferring the samples into ice and adding 200 µl of 0.3M sodium acetate, pH 5.2/0.1 mM $Na_2EDTA$/50 µg/ml yeast tRNA. The DNA was precipitated by use of 2.5 volumes of ethanol in dry ice. After centrifuging, the DNA residues were washed twice with 70% alcohol, resuspended in 200 µl of 0.3M sodium acetate, pH 5.2, and again reprecipitated with ethanol. After two washings with ethanol, the dried residues were resuspended in 50 µl of 1M piperidine and incubated at 90° C. for twenty minutes. After the cleavage by piperidine, 5 µg of yeast tRNA and 50 µl of 0.6M sodium acetate, pH 6, were added and the DNA was precipitated by ethanol. The residues were washed twice with 70% ethanol, resuspended in 100 µl of distilled water, freeze dried and resuspended in 8 µl of 83% formamide/8.3 mM $Na_2EDTA$. 4 µl of each sample, mixed with 0.5 µl of fluorescent molecular weight marker (GS2500P ROX, ABI) were loaded onto a 6% denaturing polyacrylamide gel in an automatic DNA sequencer manufactured by ABI. The results were collected and analyzed by use of the GENESCAN 772 (ABI) software.

EXAMPLE 1

Detection of mutations in the C1-inhibitor gene of patients suffering from hereditary angioedema Mutations in the C1-inhibitor gene of patients suffering from hereditary angioedema constitute a model system for the method which is the object of the present invention.

The C1-inhibitor gene is 17 kb long and consists of 8 exons. By choosing the oligonucleotide primers in the introns and close to the 5' and 3' ends of the exons, fragments of lengths of between 600 base pairs (bp) and 1000 bp can be readily obtained by amplification by the chain polymerization method, including both individual exons and groups of exons, and covering all the intron-exon boundary regions.

Exon 8 was amplified by use of primers E1 and E2 as shown in FIG. 1A which gives a schematic representation of the organization of the region containing exon 8. This figure shows that primer E1 is situated within the non-transcribed 3' region, 211 base pairs downstream of the stop codon. Primer E2 is itself situated within intron 7, 147 base pairs upstream of the first exon 8 nucleotide. The 84 codons of this exon are reproduced on the sequence of FIG. 1B.

Eight different point mutations, the majority resulting in a deterioration of the production of the C1-inhibitor protein, have been found by use of the conventional CCM technique. In addition, a permutation of G to A within codon 458 induces an already known polymorphism for the site of the Hgi AI restriction enzyme (Bock et al. (1986), Biochemistry, 25, 4292–4301). The Gln452Glu (permutation of C to G) and Pro459Arg mutations (permutation of T to G), which are linked by the dotted line in FIG. 1B, have been found on the same chromosome.

The DNA from the patient having these mutations was thus isolated to identify the partial cleavage conditions which would allow the detection of the multiple mismatches on the same DNA strand.

Figures 1, 2B:
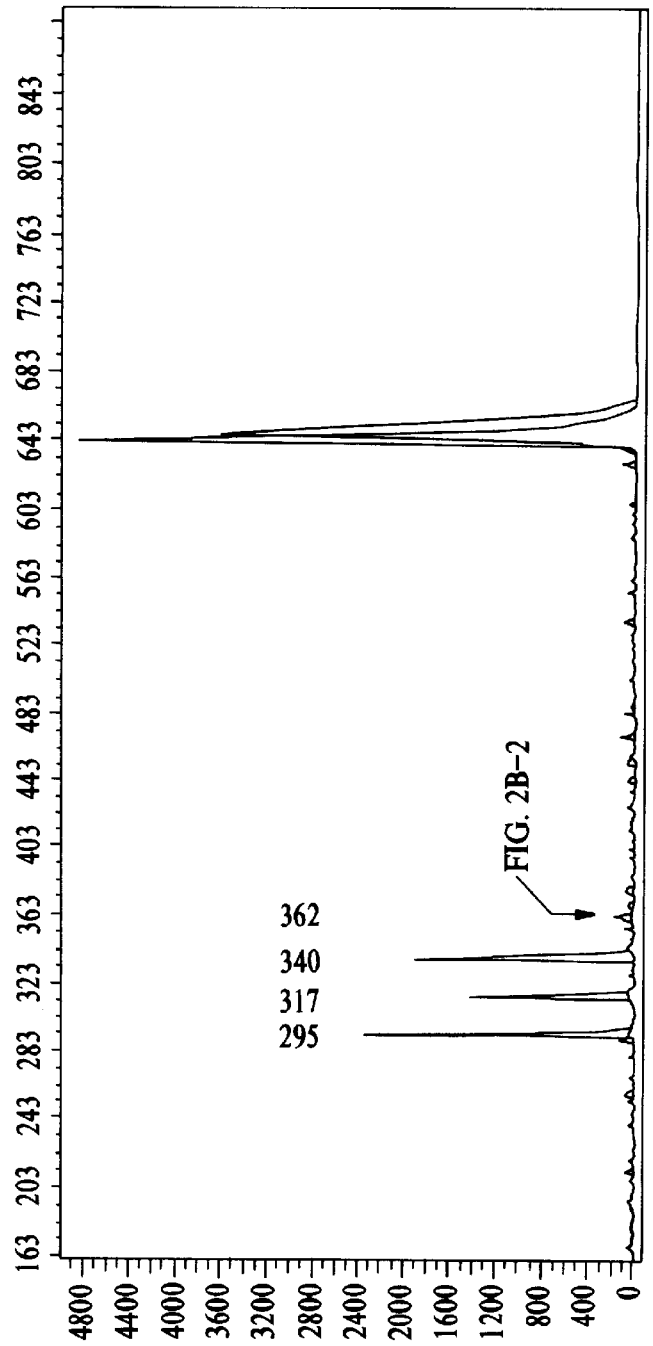
FIG. 1A represents the structure of exon 8 of the C1-inhibitor gene and neighboring regions.
FIG. 1B represents the sequence of exon 8. This sequence has been described by Tosi et al. ((1986), Gene, 42, 265–272) and Carter et al. ((1991), J. Biochem., 197, 301–308).

As shown in FIG. 2B, the hydroxylamine cleavage of non-matched C residues on the non-coding strand give rise to two peaks corresponding to sizes of respectively 295 and 317 nucleotides, as could be predicted from the types of heteroduplex molecules formed which are represented schematically in FIG. 2A. The sense strands are identified on FIG. 2A by a square representing a particular fluorescent labeling while the nonsense strands are identified by a circle corresponding to a different labeling.

The two peaks obtained show a significant intensity, in comparison with the fluorescence intensity of the non-cleaved material. It may be noted that in fact only a quarter of the DNA molecules are expected to contain the mismatch which makes the C residues easily accessible to hydroxylamine.

While the intensity of the peak at position 295 directly reflects the nature of the modification and of the cleavage, the fluorescence intensity at position 317, which is the furthest from the site of the fluorescent labeling, is weak by comparison with the expected cleavage at that site.

These results and similar ones obtained with osmium tetroxide show that the conditions used allow the detection of multiple cleavages on the same strand. In fact, the slightly milder conditions of the hydroxylamine treatment were subsequently used because of the weak cleavage on the furthest cleavage position (peak 317) and enabled cleavages of the order of 100% to be obtained.

Figures 2, 2B:
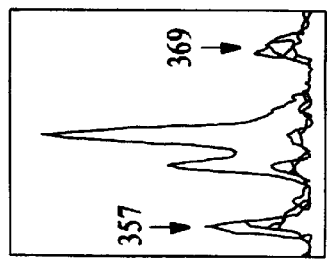

FIG. 2 also shows that redundant information is obtained by labeling the products corresponding to the two types of allele.

The strands derived from the wild type allele are represented by the heavy line in FIG. 2A, and the distances of the relevant bases from the terminal fluorescent labeling are indicated.

FIG. 2B concerns the hydroxylamine cleavage of non-matched C residues. The horizontal axis represents the size of the fragments of single DNA strands derived from coding and non-coding strands. The nucleotide size scale was obtained by use of a size marker, which was labeled with a third fluorescent dye. The vertical scale indicates the fluorescence intensities in arbitrary units.

Figure 2C:
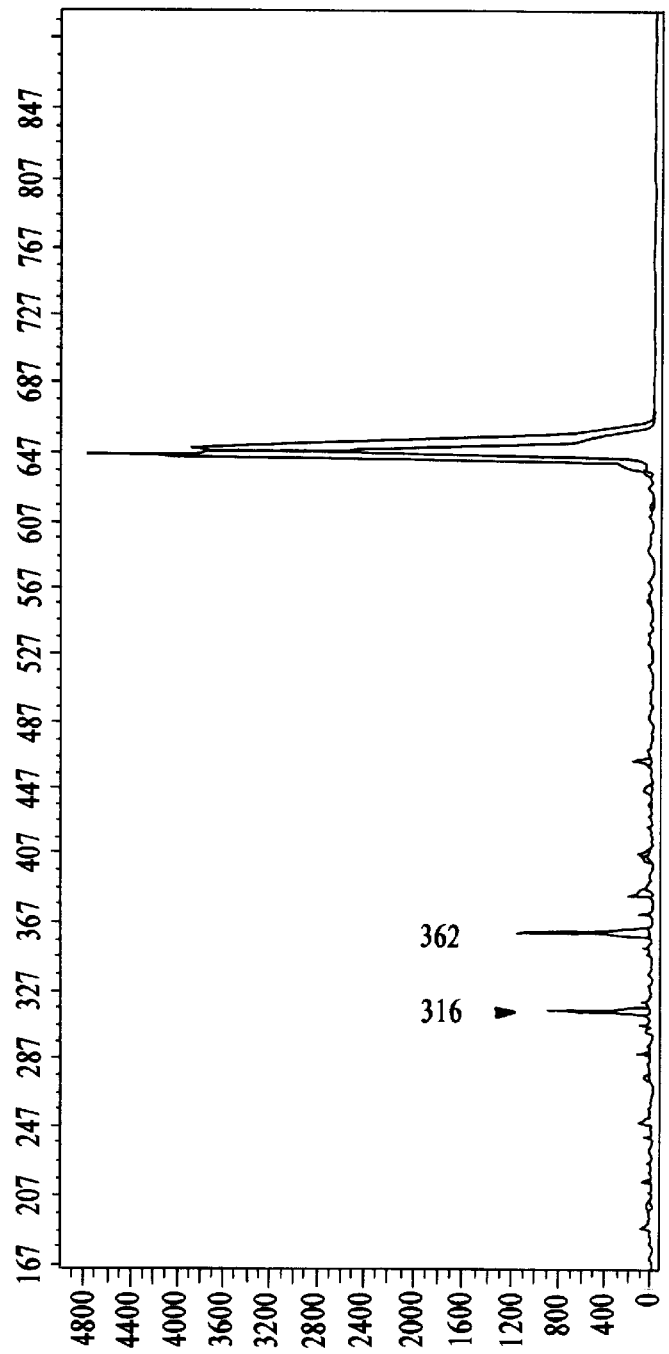

FIG. 2C shows the detection of non-matched T residues by use of osmium tetroxide.

The arrow on the figure shows a matched T residue, adjacent to the mismatch, which has nevertheless undergone significant cleavage.

In this example the two mutations, located respectively in codons 452 and 459, are revealed by a total of six distinct cleavages. Among these, two have taken place on matched bases adjacent to the mismatches. On the coding strand, the C residues have given rise to a weak but significant double peak in the presence of hydroxylamine around position 362. On the non-coding strand, the T residue has given rise, after osmium tetroxide treatment, to the peak at position 316. It may be noted that the cleavages on adjacent matched bases, although usually weaker than those obtained on non-matched bases, can take place on a half of the duplexes, and not on only a quarter, as is typically the case for mismatches containing T or C residues.

The gain in sensitivity of the detection resulting from the use of different labelings of the two DNA strands, combined with computer analysis, leads to the results shown in the inset of FIG. 2B, which represents an enlargement of the double peak around the mutation in position 362 of the coding strand, superimposed on the graph of the result obtained on the same strand for three individuals not having this mutation. It may be noted that the cleavages took place on the cytosines in positions 357 and 369.

EXAMPLE 2

Effect of the type of non-matched base and of the neighboring base composition, on the osmium tetroxide and hydroxylamine cleavages The nine mutations shown on FIG. 1 were used to study the quantitative effect of the type of non-matched base and on the neighboring base composition, on cleavages by the two reagents.

The Table shows the comparisons made from two independent experiments. While the cleavage efficiencies obtained with hydroxylamine were substantially higher than those obtained with osmium tetroxide, the nucleotide environment of the mismatches seems to have a similar effect on the two types of cleavage, since the same hierarchy of cleavage efficiencies is found for the two reagents.

Only a few mutations do not conform to this rule. For example, the Pro 476 Ser and Leu 459 Pro mutations are more sensitive to hydroxylamine modifications, owing to the presence in both cases of three consecutive cytosine residues on the cleavage site. Similarly, the relatively high cleavage rate by osmium tetroxide of the heteroduplexes on the Val451Met site is probably due to the presence of two consecutive T residues adjacent to the mismatched T. However the C.C mismatches are notable for their high sensitivity to modification, although located within a different nucleotide environment. This could be due not only to the strong cleavage by hydroxylamine but also to the strong cleavage observed in the presence of osmium tetroxide on the immediately adjacent T residues.

In the case of the Gln452 Glu mutation, the apparent asymmetry of the cleavage efficiency, depending on the strand concerned, could also be due to the presence on the non-coding strand of a C residue adjacent to a non-matched residue.

The Table also allows an estimate of the number of cleavage products which can be in general expected for each mutation, and an indication of the detection limits of the products in the case of weak cleavages.

Each mutation gives rise to at least two detectable fluorescent peaks resulting from the cleavage of the mismatched bases, but in several cases, additional information has been obtained from the cleavage of adjacent matched bases, shown in the Table by arrows.

The great majority of the cleavage products are easily detected, because of their fluorescent signal which is clearly greater than the background noise. Superimposition of the graphs as has been done for the inset to FIG. 2B is necessary only in the case of signals representing less than 10% of the cleavable double strands, such as those obtained with osmium tetroxide on the mismatches resulting from the Arg472 STOP and Val458Met mutations (Table).

Figure 3A:
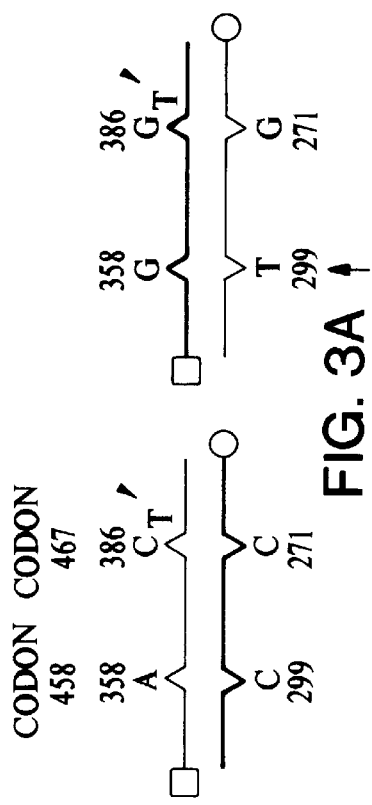
FIG. 3B represents the osmium tetroxide cleavage profile of DNA mismatches from a patient heterozygous for the Val458Met mutation.
FIG. 3C represents the same type of profile for the Pro467Arg mutation.
FIG. 3D is the profile obtained by treatment of the mismatches of FIG. 3C with hydroxylamine.
Figures 1, 3B:
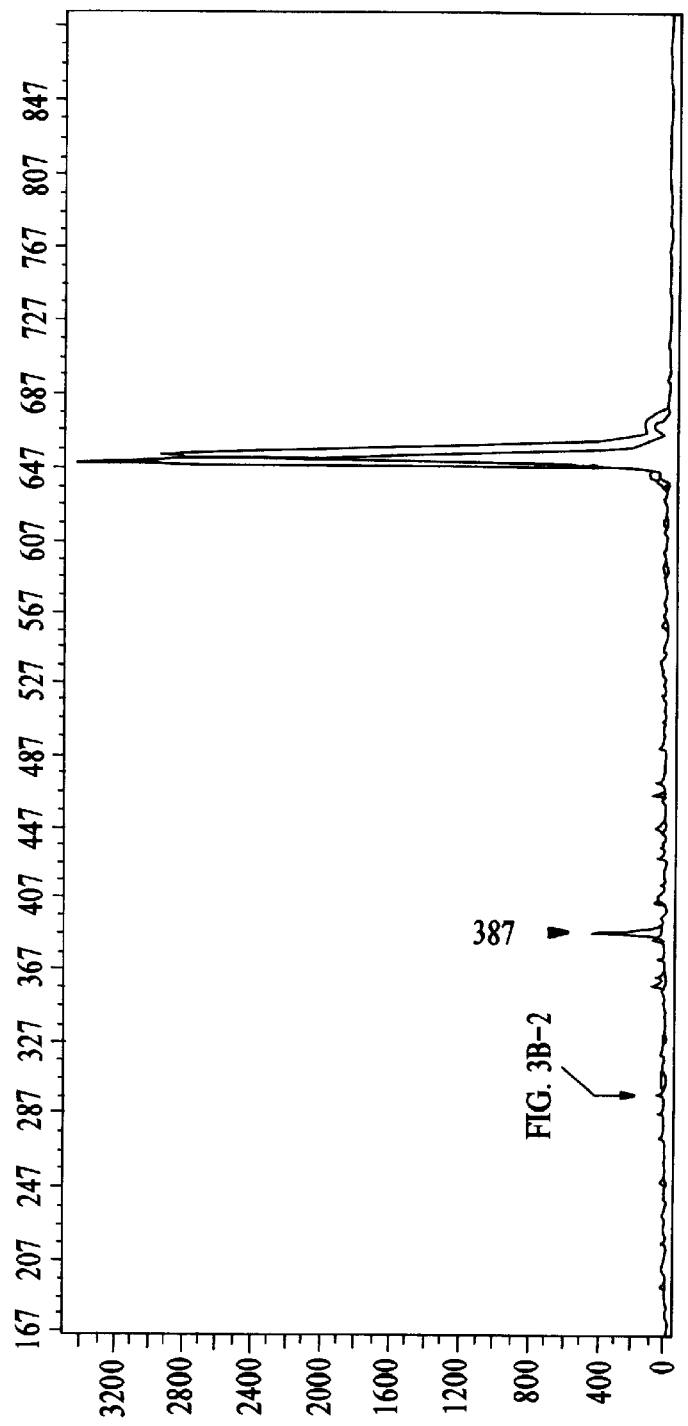
Figures 2, 3B:
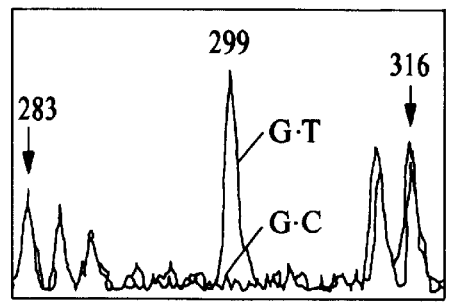
Figure 3C:
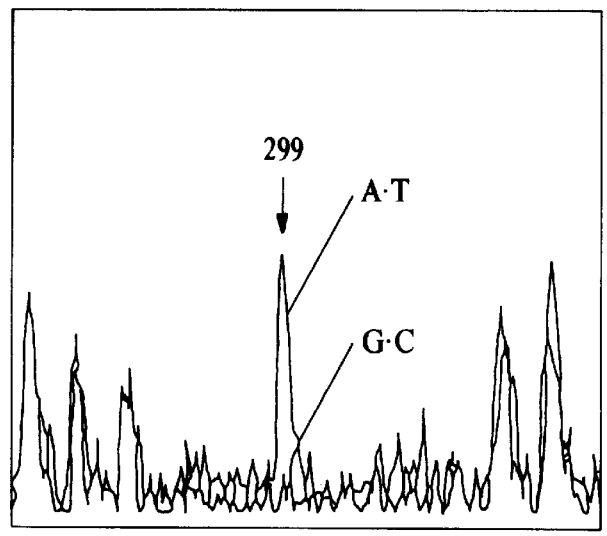

The osmium tetroxide cleavage profile for a patient heterozygous for the Val458Met mutation, which gives rise to an ineffective polymorphism, and for the pathogenic mutation Pro467Arg are shown in FIGS. 3B and 3C.

The polymorphism of the Val458Met mutation is easily detected, by treatment with hydroxylamine, and identified by a peak at the 299 position of the non-coding strand, as shown in FIG. 3A which gives a schematic representation of the part of the gene containing these two mutations.

In FIG. 3A the DNA strands represented by the thick lines are those derived from the allele having a G residue at its polymorphic site, as is most frequently the case.

Nevertheless, in the case of osmium tetroxide treatment this peak is not detected by direct measurement of the fluorescence of the non-coding strand, which carries a mismatched T at the site corresponding to this mutation (FIG. 3B). However, the coding strand has a much stronger cleavage, at position 387, due to the presence of a T residue immediately adjacent to the mismatch destabilizing C.C and G.G in half the matched molecules. In addition, a comparison of enlarged graphs of the same region in the case of treatment of DNA of other individuals with osmium tetroxide, as shown in the inset to FIG. 3B, shows that T is in fact present at the 299 position of the non-coding strand. The reactivity of this T-G mismatch with osmium tetroxide is unusually weak. This is due to the fact that the intensity of the resulting peak is only slightly greater than that of the surrounding matched T.A bases, as shown in the inset representing the non-coding strand from position 283 up to position 316.

Figure 3D:
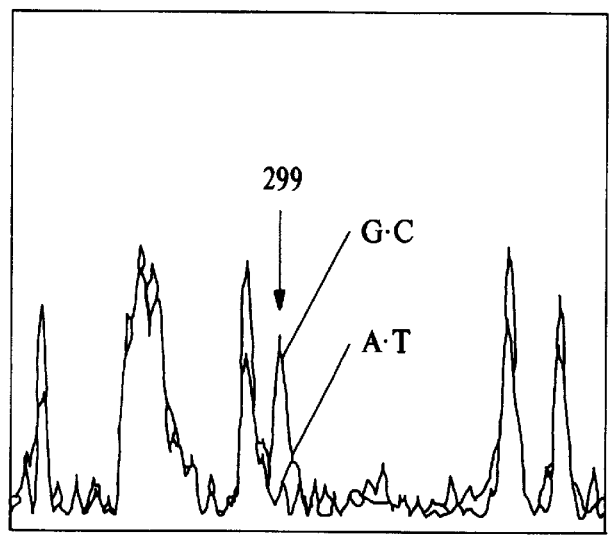

It should nevertheless be noted that this G.T mismatch is only present in one of the four duplexes. The control profile, shown in the inset, in which the peak at position 299 is not present, is that of G.C homozygous individuals at this polymorphic site. In fact, the variations between individuals, that is to say between A.T and G.C homozygotes at this polymorphic site, can be easily detected, as shown in FIGS. 3C and 3D, corresponding to the osmium tetroxide and hydroxylamine treatments respectively.

The osmium tetroxide profile (FIG. 3C) of the homozygote at position 299 is unexpectedly similar to that of the heterozygote shown in the inset of FIG. 3B, except for the peak at position 299 which is slightly smaller than that detected with the G.T mismatches. In addition the C.G homozygotes, used as uncleaved controls in FIGS. 3B and 3C, give rise to a distinct peak in the profile obtained after reaction with hydroxylamine, in contrast to the profile obtained with the A.T homozygotes (FIG. 3D). Although this example illustrates the particular case of a polymorphic site, which gives rise to appropriate genotypes for showing the difference between a cleavage of matched and non-matched bases, the appearance of a new T or C peak, absent in the profiles of other individuals, is a sufficient indication even if the amplitude of this peak is of the same order as that resulting from the cleavage of neighboring base pairs.

EXAMPLE 3

Determination of the detection threshold of the method

A patient with a double cis mutation, whose cleavage profile is shown in FIGS. 2B and 2C, gives rise to a significant number of fragments of variable intensity, which allows the detection threshold of the method to be easily tested, by diluting this material with different quantities of wild genetic material. In addition the region of the affected chromosome of this patient amplified by the enzymatic route can be determined quantitatively from serial dilutions, because Leu459Arg destroys the Hgi AI enzyme recognition site, underlined in FIG. 1.

Figure 4A:
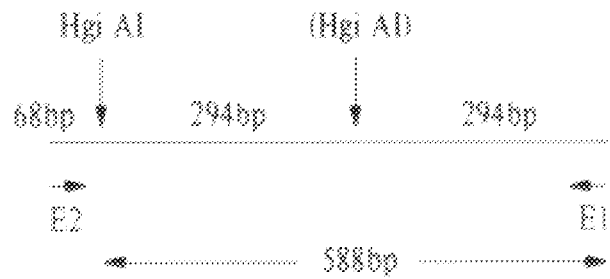
FIG. 4A represents the 588 base pair fragment containing the restriction site of the Hgi AI enzyme.

The genomic DNA of this patient was diluted with increasing quantities of normal DNA and amplified by the enzymatic route. The importance of the chromosome carrying these mutations was verified, after the first amplification by chain polymerization (PCR), by studying the disappearance in serial dilutions of the fragment of 588 base pairs shown in FIG. 4A, which is resistant to digestion by the Hgi AI enzyme. Aliquots of each serial dilution were then subjected to chemical modifications with osmium tetroxide and hydroxylamine.

Figure 4B:
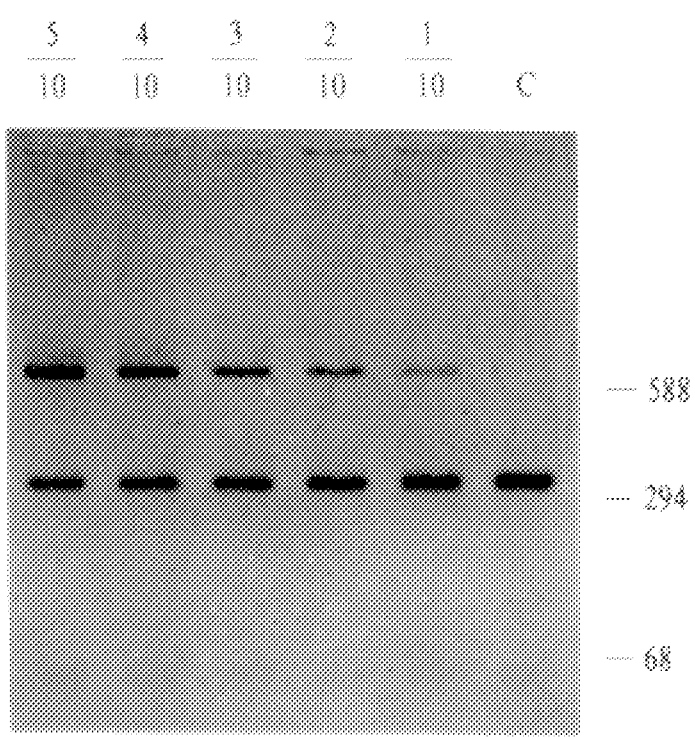
FIG. 4B is a photograph of a migration gel of the hydroxylamine treatment products of matches between the wild allele and the allele of a patient with a double cis mutation in the fragment shown in FIG. 4A, at different dilutions.

FIG. 4B shows that up to a dilution of the DNA by a factor of five, in other words one chromosome carrying the mutation per ten chromosomes, the mismatches were readily detected.

In order to simplify the figures, we have illustrated only the hydroxylamine cleavage of the non-coding strand, for diluted and undiluted DNA, since dilutions of similar intensity were measured, after dilution, in the other cleavage profiles of FIG. 2.

FIG. 4B is a gel on which the different dilutions of DNA and the control wild type DNA (well C) are shown.

Figure 4C:
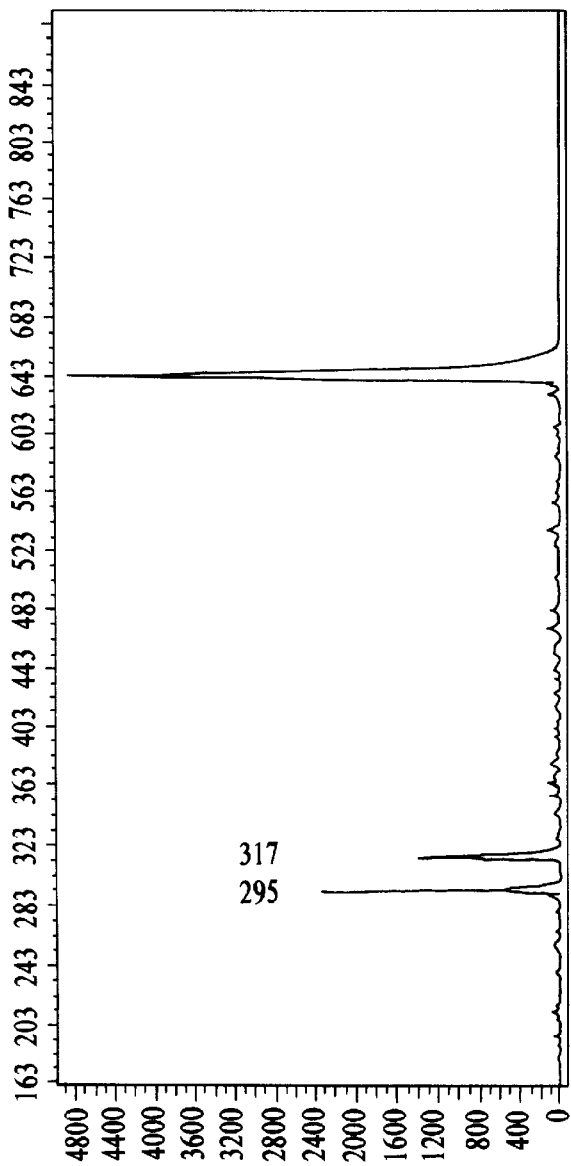
FIG. 4C represents the profile after hydroxylamine treatment of the cleavage products of the non-coding strand in a situation where the DNA has not been diluted.

FIG. 4C represents the profile of the non-coding strand, after treatment of the DNA with hydroxylamine, for the heterozygous patient and in a situation where the DNA has not been diluted.

Figure 4D:
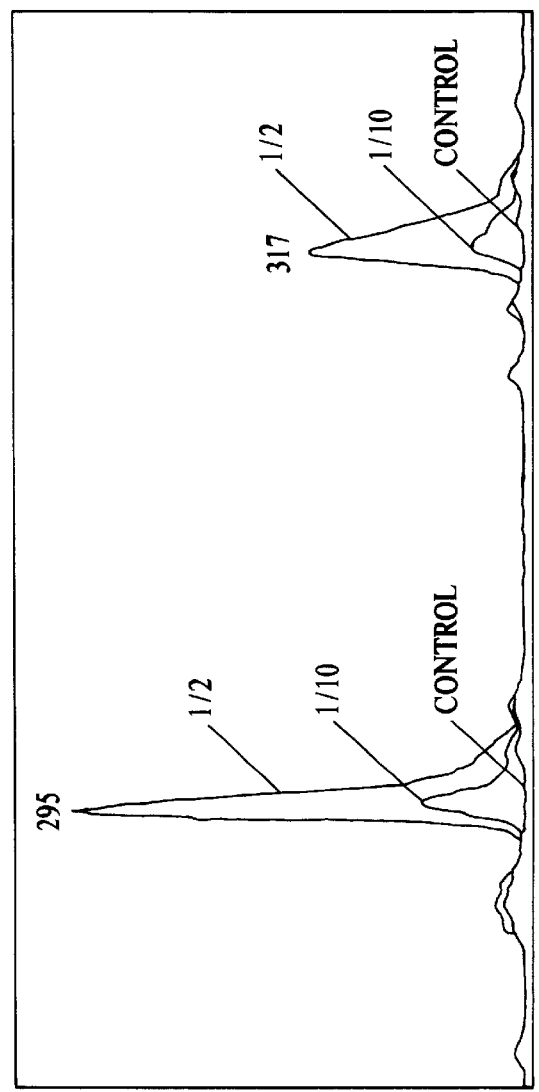
FIG. 4D is an enlargement of the regions containing the peaks in positions 295 and 317 of FIG. 4C, at different dilutions.

FIG. 4D is an enlargement of the region containing the peaks in positions 295 and 317. On this figure are shown the intensities of the peaks at a dilution of a half (½), one tenth (1/10) and the intensity of the spectrum obtained with the control DNA from a wild type individual.

Even the double peak obtained with hydroxylamine for the coding strand around position 362 (cf. inset of FIG. 2A) is detectable, at a dilution of 1/10 of the chromosome.

CONCLUSION

The results of these examples of the use of the invention clearly show that the method which is the object of the present invention enables the reliable and sensitive determination of the presence and the position of base substitutions in nucleotide sequences.

This detection is made possible by the differential double labeling of the two strands, using fluorescent labels.

The method which is the object of the present invention is in addition performed more rapidly than the conventional CCM method, and also has the advantage of using stable fluorescent labeling products.

The method which is the object of the present invention in addition differs from the methods described in the state of the art in that:

it enables a large number of mismatches, and thus information, to be obtained in an optimal manner, as a result of the labeling of the mutant allele, the coding and non-coding strands are labeled differently, which thus reduces to a minimum the number of chemical reactions and leads to a precise location of the mutations, the specific background noise of a given strand during cleavages at a given position is highly reproducible and renders detectable mismatches which are ordinarily poorly cleaved, such as homozygous polymorphisms, as is shown on FIG. 3. Thus, by using the background noise of the cleavages as a reference sequence, the mutation can be precisely sequenced, to within one nucleotide.

The particularly high sensitivity of the method which is the object of the present invention should enable determination of the presence and the position of base substitutions in homozygous and heterozygous individuals, in the case of hereditarily transmitted characteristics, but also detection of somatic mutations in which the chromosome on which the mutation has taken place is diluted within a large number of chromosomes carrying a wild allele, which is in no way possible with the methods described in the state of the art.

TABLE

Comparison of the base environment on mismatch cleavage

| | HYDROXYLAMINE | | | | OSMIUM TETROXIDE | | |
| | | cleavage[a] | | | | cleavage[a] | |
| Mutation | Mismatch | Exp 1 | Exp 2 | Mutation | Mismatch | Exp 1 | Exp 2 |
|---|---|---|---|---|---|---|---|
| Arg472stop | GGGG$^G$GAGT CCCC$_A$CTCA | 24 | 21 | Arg472stop | GGGG$^T$GAGT CCCC$_G$CTCA | <1 | <1 |
| Val458Met | CTTC$^A$TGCT GAAG$_C$ACGA | 40 | 34 | Val458Met | CTTC$^G$TGCT GAAGTACGA | 9 | 4 |
| Val451Met | TGAA$^A$TGCA ACTT$_C$ACGT | 43 | 40 | Pro476Ser[b] | TGAC$^T$CCAG ACTG$_G$GGTC | 10 | 8 |
| Phe455Ser | CCCT$^C$CCTC GGGA$_A$GGAC | 50 | 53 | Phe455Ser[b] | CCCT$^T$CCTC[b] GGGA$_G$GGAC | ND[c] | 8 |
| Leu459Arg | GTGC$^T$CTGG CACG$^C$GACC | 57 | 49 | Leu459Pro[b] | GTGC$^T$CTGG CACG$_G$GACC | 23 | 11 |
| Pro476Ser | TGAC$^C$CCAG ACTG$_A$GGTC | 56 | 58 | Val451Met[b] | TGAA$^G$TGCA ACTT$_T$ACGT | 34 | 19 |
| Leu459Pro | GTGC$^C$CTGG CACG$_A$GACC | 61 | 62 | Leu459Arg[b] | CACG$_C$GACC CACGCGACC | 43 | 31 |
| Gln452Glu | AGTG$^C$AGCA[d] TCAC$_C$TCGT | 67 | 66 | | | | |
| Pro467Arg | TTCC$^C$TGTC[d] AAGG$_C$ACAG | 82 | 79 | | | | |
| Pro467Arg | TTCC$_C$TGTC[d] AAGG$_C$ACAG | 84 | 84 | | | | |
| Gln452Glu | AGTGCAGCA[d] TCAC$_C$TCGT | 100 | 89 | | | | |

[a]Expressed as the percentage of the potentially cleavable molecules theoretically present. These percentages are calculated as the ratio of the fluorescence measured for the cleaved products to a quarter of the total DNA and corrected, when the same strand is cleaved at two sites, for the effect of the proximal cleavage on the intensity observed for the distal cleavage.
[b]Mismatches detected by superimposing the graphs.
[c]Not performed for this series. In other experiments, the extent of the modifications induced by osmium tetroxide was similar to that induced by the Pro476Ser mutation.
[d]Cleavages by osmium tetroxide on the adjacent T residues were detected.

SEQUENCE LISTING

We claim:

1. A method for detecting the presence of base substitutions or deletions in a nucleotide sequence contained in a preparation of double-stranded DNA to be tested in which:

the region containing the nucleotide sequence of the DNA strand to be tested and a second DNA strand of known sequence, which serves as a reference DNA strand for comparison with the DNA strand to be tested, is specifically amplified and the sense and nonsense strands of these DNAs are labeled with different fluorescent labels or other non-isotopic labels, the amplified DNAs are hybridized, and the heteroduplexes formed are detected by cleavage of the mismatched parts of the strands.

2. A method for detecting the presence of base substitutions or deletions in a nucleotide sequence contained in a preparation of heterozygous or heterogenous double-stranded DNA to be tested in which:

the region containing the nucleotide sequence of the DNA to be tested is specifically amplified and the sense and nonsense strands of this DNA are labeled with different fluorescent labels or other non-isotopic labels, the amplified DNAs are hybridized, and the heteroduplexes formed are detected by cleavage of the mismatched parts of the strands.

3. The method according to claim 2, wherein the heterogenous DNA is composed of a mixture of DNA from two variants of a bacteria or of DNA extracted from tumor mosaic cells.

4. The method according to claim 1, wherein the DNA to be tested and the known DNA are amplified in the same preparation.

5. The method according to any one of claims 1 through 4, wherein the reagent cleaving the mismatched parts is a chemical reagent.

6. The method according to any one of claims 1 through 4, wherein the reagent cleaving the non-matched parts is an enzyme.

7. The method according to any one of claims 1 through 4, wherein the heteroduplexes are, prior to their detection, concentrated by passage over a support that specifically retains them.

8. The method according to any one of claims 1 through 4, wherein the DNAs containing the nucleotide sequence to be determined are amplified by the chain polymerization method using two primers located at the two ends of the sequence to be amplified.

9. The method according to claim 8, wherein the two primers are labeled respectively with different fluorescent labels.

10. The method according to any one of claims 1 through 4, wherein the size of the double-stranded DNA molecule containing the nucleotide sequence is between 150 and 10,000 base pairs.

11. The method according to claim 5, wherein the heteroduplexes are, prior to their detection, concentrated by passage over a support which specifically retains them.

12. The method according to claim 6, wherein the heteroduplexes are, prior to their detection, concentrated by passage over a support which specifically retains them.

13. The method according to claim 5, wherein the DNAs containing the nucleotide sequence to be determined are amplified by the chain polymerization method using two primers located at the two ends of the sequence to be amplified.

14. The method according to claim 6, wherein the DNAs containing the nucleotide sequence to be determined are amplified by the chain polymerization method using two primers located at the two ends of the sequence to be amplified.

15. The method according to claim 7, wherein the DNAs containing the nucleotide sequence to be determined are amplified by the chain polymerization method using two primers located at the two ends of the sequence to be amplified.

16. The method according to claim 5, wherein the size of the double stranded DNA molecule containing the nucleotide sequence is between 150 and 10,000 base pairs.

17. The method according to claim 6, wherein the size of the double stranded DNA molecule containing the nucleotide sequence is between 150 and 10,000 base pairs.

18. The method according to claim 7, wherein the size of the double stranded DNA molecule containing the nucleotide sequence is between 150 and 10,000 base pairs.

19. The method according to claim 8, wherein the size of the double stranded DNA molecule containing the nucleotide sequence is between 150 and 10,000 base pairs.

20. The method according to claim 9, wherein the size of the double stranded DNA molecule containing the nucleotide sequence is between 150 and 10,000 base pairs.

21. A method for detecting the presence and the position of base substitutions or deletions in a nucleotide sequence contained in a preparation of double-stranded DNA to be tested in which:

the region containing the nucleotide sequence of the DNA strand to be tested and a second DNA strand of known sequence is specifically amplified, and the sense and nonsense strands of these DNAs are labeled with different fluorescent labels or other non-isotopic labels, the amplified DNAs are hybridized, the heteroduplexes formed are detected by cleavage of the mismatched parts of the strands, and the location of the mismatch or mismatches is determined using the background noise of the cleavages as a reference sequence.

22. A method for detecting the presence and the position of base substitutions or deletions in a nucleotide sequence contained in a preparation of heterozygous or heterogenous double-stranded DNA to be tested in which:

the region containing the nucleotide sequence of the DNA to be tested is specifically amplified and the sense and nonsense strands of this DNA are labeled with different fluorescent labels or other non-isotopic labels, the amplified DNAs are hybridized, the heteroduplexes formed are detected by cleavage of the mismatched parts of the strands, and the location of the mismatch or mismatches is determined using the background noise of the cleavages as a reference sequence.

23. The method according to claim 6, wherein the enzyme is MutY.

24. The method according to claim 5, wherein the chemical reagent is hydroxylamine.

25. The method according to claim 5, wherein the chemical reagent is osmium tetroxide.

* * * * *